Figure 1:
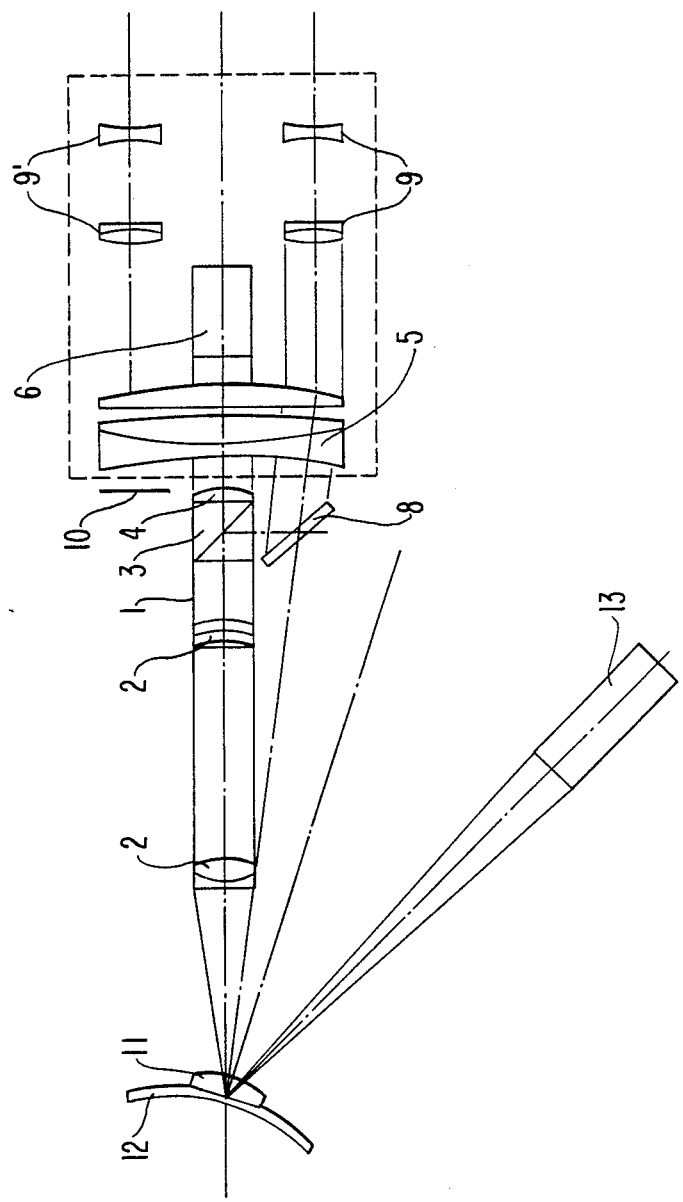

United States Patent [19]

Reis

[11] Patent Number: 4,976,535
[45] Date of Patent: Dec. 11, 1990

[54] ENDOTHELVORSATZ

[75] Inventor: Werner Reis, Munich, Fed. Rep. of Germany

[73] Assignee: G. Rodenstock Instrumente GmbH, Ottobrunn-Riemerling, Fed. Rep. of Germany

[21] Appl. No.: 346,224

[22] Filed: May 2, 1989

[30] Foreign Application Priority Data

May 2, 1988 [DE] Fed. Rep. of Germany ....... 3814866

[51] Int. Cl.$^5$ .............................................. A61B 3/10
[52] U.S. Cl. .................................. 351/214; 351/216; 351/219
[58] Field of Search ............... 351/214, 216, 219, 205, 351/211, 212

[56] References Cited

U.S. PATENT DOCUMENTS 4,711,541 12/1987 Yoshino et al. ...................... 351/214
4,744,649 5/1988 Niino et al. ......................... 351/214

Primary Examiner—Paul M. Dzierzynski
Attorney, Agent, or Firm—Antonelli, Terry, Stout & Kraus

[57] ABSTRACT

An endothelium attachment for a slit lamp device with a microscope objective to increase the magnification of the slit lamp microscope which can be attached in front of the slip lamp microscope housing. The attachment includes a beam splitter provided between the microscope objective and the primary objective of the slit lamp microscope, this beam splitter being arranged in the optical axis of the primary objective and deflecting at least a portion of the light reflected by the eye to be examined into at least one ocular beam path of the slit lamp microscope, and that the portion of the light passing through the beam splitter impinges upon a measuring and/or recording unit.

11 Claims, 2 Drawing Sheets

ENDOTHELVORSATZ

The invention relates to an endothelium attachment for a slit lamp device.

Endothelium attachments permit vital microscopy of the corneal endothelium and its neighboring structures in the various primary and secondary endotheliopathies by the so-called corneal reflected-light microscopy. Thereby, reflected-light microscopy becomes an important instrument for early diagnosis, differential diagnosis, and progressive observation. This method affords a decision aid in endothelium-traumatizing first and repeated interventions and is moreover of significance for evaluation of donor material.

For this reason, a great variety of instruments have been developed for the so-called corneal reflected-light microscopy. In this context, reference is invited to the overview article by CH. Hartmann in "Fortschritte der Ophthalmologie" [Advances in Ophthalmology], 1987, pp. 313-322.

By the way, reference is had to this overview article for explanation of all terms not described in detail herein and, in particular, for explaining the expressions "noncontact method" and "contact method".

In case of a physician having a well-established practice, of importance are not so much the "stand-alone reflected-light microscopes" serving especially for research purposes, but rather accessories for the slit lamp which latter is present in any ophthalmologist's practice.

Thus far, a great variety of endothelium attachments for slit lamp devices have become known, and, respectively, the corresponding attachments by the companies Zeiss and Topcon. These attachments have the feature in common that when utilizing the endothelium attachment, the so-called primary objective of the slit lamp microscope must be removed. The central beam path is divided into two secondary beam paths by the attachment. As a result, the microscopic image can be photographed only with the use of a beam splitter after the magnification changer. Thereby an undesirable lengthening of the slit lamp apparatus results. Furthermore, the attachment can be corrected only in a very expensive model so that it is suitable as a measuring attachment.

The invention is based on the object of further developing an endothelium attachment for a slit lamp device in such a way that observation as well as simultaneous measurement and/or recording are possible without having to lengthen the slit lamp device in, its dimensions.

According to the invention, the endothelium attachment is adapted without restructuring the slit lamp instrument, i.e. without removal of the primary objective of the instrument. Thus, the attachment serves merely for preliminary magnification whereas the actual measuring beam path passes through the middle of the primary objective and thus is imaged extensively without optical imaging errors and distortions.

As a consequence, the endothelium attachment according to this invention has not only the advantage that there is no increase in the total length of the device by the attachment mounted between the primary objective and the chin rest for the test person's head, but also the advantage that even without expensive corrective measures, an extensively fault-free measuring beam path is realized.

According to a feature of invention, a compensating lens is utilized for the adjustment of differing optical path lengths in the actual measuring beam path and in the observation beam path reflected in an ocular beam peath decentered with respect to the primary objective. By means of such a lens, typically having a refractive power of 1 diopter, the sharp focusing of the measuring beam path by way of the observation beam path is facilitated.

A further feature simplifies the structure of the beam splitter since a simple beam splitter can be used reflecting light into an ocular beam path merely in one direction from the measuring beam path. In order to prevent appearance of interfering images in the other ocular beam path in case of binocular viewing into the slit lamp microscope, a diaphragm is inserted in this beam path by the endothelium attachment constructed in accordance with this invention.

In principle, a great variety of different devices can be utilized as the measuring and/or recording unit, for example scales, polaroid cameras, miniature cameras, or the like. However, the use of a TV camera, and particularly a small CCD camera is especially advantageous, since such a camera not only permits observation of the endothelium image but also a software-mode further processing of the scale image.

The endothelium attachment according to this invention can, be utilized in the so-called contact method as well as in the so-called noncontact method. For use in the so-called noncontact method, it is merely necessary to swing the spring-loaded contact element out of the beam path.

Moreover, according to another feature, the endothelium attachment according to this invention can be readily utilized for the evaluating measurement of donor eyes.

The utilization of a soft contact lens as an "intermediate element" between the contact element and the eye has the advantage that the eye which, in principle, is very sensitive to pressure, need not be anesthetized for measurement. The soft contact lens does not interfere with the actual measuring step—as has been perceived according to this invention. The advantages of using a soft contact lens become apparent, in particular, in the endothelium attachment of this invention since such an attachment can be quickly retrofitted to a slit lamp instrument. Precisely in a quickly retrofittable attachment, it is of special significance for the examining personnel if the eye need not be anesthetized before the endothelial measuring step is carried out.

Figure 2:
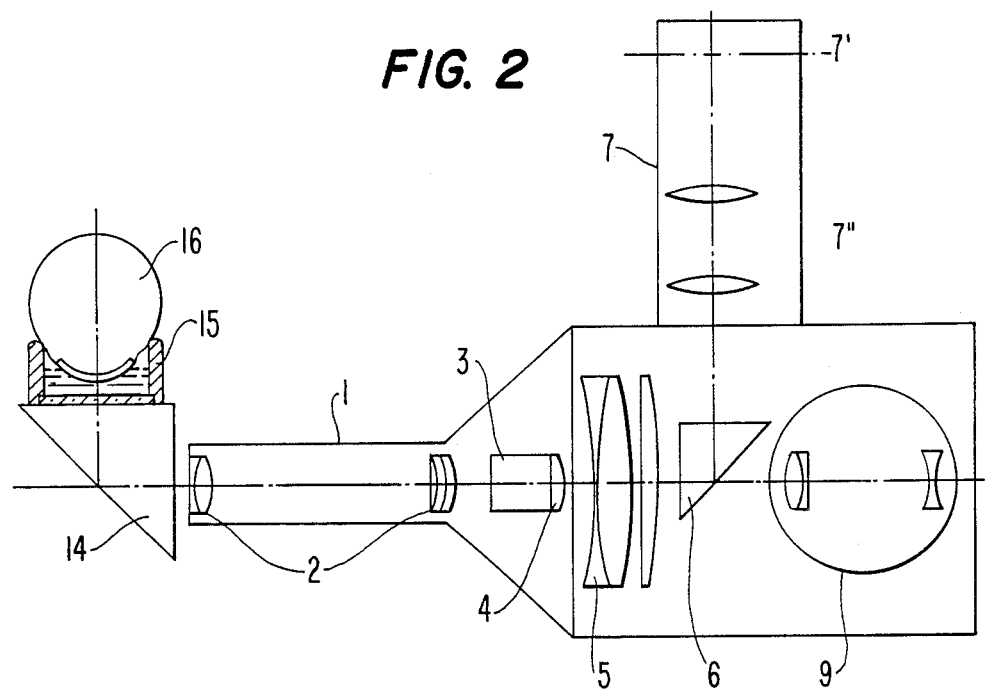
Figure 3A:
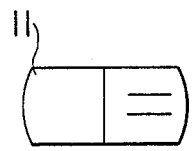
Figure 3B:
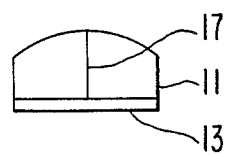
Figure 3C:
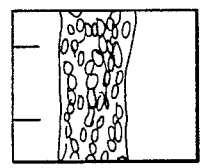

The invention will be described in greater detail below with the aid of an embodiment, referring to the drawings wherein:

FIG. 1 is a top view of an endothelium attachment with a conventional slit lamp microscope, FIG. 2 is a lateral view of the endothelium attachment while measuring donor eyes, and FIGS. 3a and 3b show a top and side view, respectively, of a contact element utilized in accordance with this invention, and FIG. 3c shows a monitor image of the contact element in use.

The endothelium attachment illustrated in FIG. 1 exhibits, in a tube 1, a microscope objective 2, a 1:1 splitter cube 3, as well as a compensating lens 4 mounted to the splitter cube 3.

The light passing through the splitter cube 3 travels through a primary objective 5 of the actual slit lamp microscope and is deflected by a deflecting prism 6 in the upward direction to a measuring and recording unit 7 which, in the illustrated example of FIG. 2, is a CCD camera with an image plane 7' and a zoom objective 7".

The light reflected by the splitter cube 3 is deflected by a mirror 8 in a decentered fashion to the primary objective 5 and passes through the latter into the "normal" ocular beam path of the ocular 9.

Furthermore, the endothelium attachment comprises a diaphragm 10 covering the other ocular beam path 9'.

In the embodiment illustrated in FIG. 1, the endothelium attachment of this invention is utilized for measurement in the so-called contact method. For this purpose, a contact element 11 is applied to an eye 12 with a contact pressure of, for example, 20 mm Hg column. Numeral 13 denotes the deflecting prism of a slit lamp which illuminates the contact element 11. The angle between the illumination and observation beam paths is in this arrangement customarily 45°.

The endothelium attachment of this invention can be threaded in place in front of the primary objective without modifying the housing of the slit lamp microscope. The magnification range at the monitor can be adjusted, for example, to have a variability of between 100- and 250-fold by the use of a CCD camera with a zoom objective having, for example, a focal length range from 16 to 100 mm.

With the aid of the Galilean changer installed in conventional slit lamp instruments, it is possible to set, with a 10-fold ocular magnification, the magnifications of 50-fold, 100-fold and 200-fold in the observation beam path.

When using the instrument in the so-called contact method, it is preferred to print a linear marking onto the contact element as illustrated in top and side view in FIGS. 3a and 3b. This linear marking also appears on the monitor picture and can be set with an external scale to an exact desired value as shown in FIG. 3c. The possible optical or mechanical tolerances that can result between the endothelium image and the monitor picture are thus eliminated. The projected-in marking can moreover be further processed also in software mode, there being no necessity for an external comparison scale. In this connection, it is especially advantageous to minimize reflections by means of a black stripe 17 in the contact element.

When using the device in the so-called noncontact method, the resilient contact element 11 is merely pulled off the attachment. Compensation of the imaging scale can be effected by swinging an auxiliary lens into the microscope part, or this compensation can be determined by means of an attachable tube with a grating plate (instead of the tube with contact element) at the monitor. In this usage, the procedure is as follows:

Focusing of endothelium and determination of optimum image, observation at the monitor.

Attachment of grating plate tube and manual or software-mode determination of the imaging scale.

Evaluation of image.

In the lateral view of the endothelium attachment illustrated in FIG. 2, a further usage possibility is depicted (in a deviation from FIG. 1), namely the surveying of donor eyes. For this purpose, a deflecting prism 14 is attached, for example, to the headrest, not shown, of the slit lamp instrument; a cuvette with glass plate and linear marking (reference numeral 15), filled with a liquid, is placed onto this deflecting prism. The actual donor eye 16 is placed onto this cuvette. The endothelium is positioned with the cross slide of the slit lamp instrument. The imaging scale is then adjustable at the monitor by means of the linear marking at the cuvette.

The invention has been described above with reference to an embodiment without limiting the general idea of this invention; of course, a great variety of modifications are possible within this idea.

Thus, in place of a simple 1:1 beam splitter, the use of a more complicated beam splitter is likewise feasible, reflecting component beam paths into both ocular beam paths.

Moreover, the engraved scale on the contact element, mixed into the projection of the monitor, can be evaluated not only manually but also in a software mode by image processing. In this connection, FIG. 3c shows the corresponding monitor picture.

In any event, it is possible on account of the thus-attained elimination of the mechanical and optical tolerances, by using the concomitantly projected scale, to utilize commercially available parts, such as, for example, conventional zoom objectives which need not be specially selected, for setting the optimum magnification at the monitor.

However, above all, changing of the imaging scale does not require a change of the objective.

Moreover, in the attachment of this invention, the resilient contact element is simply placed onto the so-called noncontact optic.

In order to be able to exploit the advantages of the attachment of this invention, adaptable in a few seconds to a slit lamp instrument, in daily practice, it is especially advantageous to insert, between the small contact element and the cornea, a soft contact lens without optical effect having a defined thickness and diameter (about 8–10 mm). Thereby, the contact element can be placed against the cornea, which is very sensitive to touch, without anesthetizing; in this procedure, there are no painful irritations arising during contact with the attachment. Neither is the epithelial tissue injured by the contact pressure and the shifting of the contact element on the cornea, necessary for adjustment. However, above all, inasmuch as no anesthetizing is required, working with the endothelium attachment of this invention is possible also for users who are not permitted to perform anesthesia.

I claim:

1. An endothelium attachment for a slit lamp device including microscope means having a primary objective and at least one ocular beam path for enabling observation of an eye to be examined, the endothelium attachment comprising means for detachable mounting on a housing of the slit lamp microscope means for increasing the magnification of the slit lamp microscope means, the magnification increasing means including a microscope objective positionable in front of the primary objective of the slit lamp microscope means between the eye to be examined and the primary objective, and beam splitter means provided between the microscope objective and the primary objective of the slit lamp microscope means, the beam splitter means being disposed along an optical axis of the primary objective of the slit lamp microscope means for deflecting a portion of light reflected by the eye to be examined into the at least one ocular beam path of the split lamp microscope means so that a portion of the light passing through the beam splitter means impinges upon at least one of a measuring and recording means.

2. An endothelium attachment according to claim 1, wherein the magnification increasing means further includes compensating lens means being disposed in the beam path of the light passing through the beam splitter means for enabling adjustment for differing optical path lens in a measuring beam path and an observation beam path.

3. An endothelium attachment according to claim 1 or 2, wherein the slit lamp microscope means includes two ocular beam paths and further comprising means arranged for reflecting light from the beam splitter means into only one of the two ocular beam paths, and diaphgram means arranged so that light from the beam splitter means is not reflected along the other of the two ocular beam paths.

4. An endothelium attachment according to claim 1, wherein a recording means is provided, the recording means including a video camera having a zoom optic.

5. An endothelium attachment according to claim 1, further comprising a contact element arranged for contact with the eye to be examined for enabling endothelium measurement in accordance with a contact method, the contact element having a scale applied thereon.

6. An endothelium attachment according to claim 5, further comprising a soft contact lens insertable between the contact element and the eye to be examined.

7. An endothelium attachment according to claim 5, further comprising a grating plate mountable to the contact element.

8. An endothelium attachment according to claim 5, further comprising means for introducing grating plates into the measuring beam path.

9. An endothelium attachment according to claim 1, further comprising means for projecting a scale into the beam path of the reflected light in accordance with a non-contact method.

10. An endothelium attachment according to claim 1, further comprising a cuvette for receiving the eye to be examined, the cuvette being arranged for positioning in front of the microscope objective.

11. An endothelium attachment according to claim 1, wherein both a contact method and a non-contact method is utilized, and means for compensating for differences in the optical path length is enabled upon transition from the contact method to the non-contact method.

* * * * *